United States Patent [19]

Stein et al.

[11] Patent Number: 5,545,626
[45] Date of Patent: Aug. 13, 1996

[54] METHOD OF TREATING GLAUCOMA WITH OLIGONUCLEOTIDES

[75] Inventors: Cy A. Stein, New City, N.Y.; Martin B. Wax, Chesterfield, Mo.

[73] Assignees: The Trustees of Columbia University in the City of New York, New York, N.Y.; Washington University, St. Louis, Mo.

[21] Appl. No.: 184,223

[22] Filed: Jan. 19, 1994

[51] Int. Cl.$^6$ ................................................. A61K 31/735
[52] U.S. Cl. ............................................. 514/44; 514/913
[58] Field of Search ...................................... 514/44, 913

[56] References Cited

U.S. PATENT DOCUMENTS 5,320,962  6/1994  Stiles et al. ......................... 435/252.3

OTHER PUBLICATIONS

Crosson. *Current Eye Research.* 11 (5):453–458. "Ocular Hypotensive Activity of the Adenosine Agonist . . ." 1992.

Loke et al. *Proc Nat'l Acad Sci. USA.* 86:3474–3478. "Characterization of oligonucleotide transport into living cells." May 1989.

Bowman, E.J., et al. (1988) "Bafilomycins: A class of Inhibitors of Membrane ATPases from Microorganisms, Animal Cells, and Plant Cells", Proc. Natl. Acad. Sci. U.S.A. 85:7972–7976 (Exhibit 2).

Harvey, W. R. (1992) "Physiology of V–ATPases", J. Exp. Biol. 172:1–17 (Exhibit 3).

Iversen, P. (1991) "In Vivo Studies With Phosphorothioate Oligonucleotides: Pharmacokinetics Prologue", Anti–Cancer Drug Design 6:531–538 (Exhibit 4).

Mellman, I., et al. (1986) "Acidification of the Endocytic and Exocytic Pathways", Ann. Rev. Biochem 55:663–700 (Exhibit 5).

Morimaya, Y., and Nelson, N. (1988) "Inhibition of Vacuolar $H^+$–ATPases by Fusidic Acid and Suramin", FEBS Let. 234:383–386 (Exhibit 6).

Nelson, R. D. et al. (1992) "Selectively Amplified Expression of an Isoform of the Vacuolar $H^+$–ATPase 56–Kilodaton Subunit in Renal Intercalated Cells" Proc. Natl. Acad. Sci. U.S.A. 89:3541–3545 (Exhibit 7).

Stein, C. A., and Cheng, Y.—C. (Aug. 1993) "Antisense Oligonucleotides as Therapeutic Agents–Is the Bullet Really Magical?", Science 261:1004–1012 (Exhibit 8).

Uhlmann, E., and Peyman, A. (1990) "Antisense Oligonucleotides: A New Therapeutic Principle", Chemical Reviews 90:543–584 (Exhibit 9).

Wax, M. (1992) "Signal Transduction in the Ciliary Epithelium", Pharmocology of Glaucoma, Williams & Wilkins, Baltimore pp. 84–210 (Exhibit 10).

Yilla, M., et al. (Sep. 1993) "Involvement of the Vacuolar $H^+$–ATPases in the Secretory Pathway of HepG2 Cells", J. Biol. Chem. 268–19092–19100 (Exhibit 11).

*Primary Examiner*—S. Mark Clardy
*Attorney, Agent, or Firm*—John P. White

[57] ABSTRACT

The present invention provides a method of treating glaucoma which comprises administering to a subject an effective amount of an oligonucleotide which may be substituted or modified in its phosphate, sugar, or base, so as to decrease intraocular pressure and thereby treat the glaucoma.

22 Claims, 12 Drawing Sheets ciliary process tip ciliary process crypt ciliary process tip
+ iso/- prop ciliary process tip
+ iso/+ prop ciliary process crypt
+ iso/- prop ciliary process crypt
+ iso/+ prop ciliary process tip
+ PDBu ciliary process tip
+ 4αPDD ciliary process crypt
+ PDBu ciliary process crypt
+ 4αPDD

FIGURE 6

| DRUG TREATMENT | CILIARY TIP | | | CILIARY CRYPT | | |
|---|---|---|---|---|---|---|
| | Total Cells | % Stained | % Unstained | Total Cells | % Stained | % Unstained |
| Control | 194 | 83 | 17 | 536 | 30 | 70 |
| Isoproterenol 1μM | 274 | 86 | 14 | 297 | 80 | 20 |
| ISO 1μM + prop 1μM | 142 | 74 | 26 | 250 | 39 | 61 |
| Phorbol dibutyrate 1μM | 301 | 82 | 18 | 373 | 74 | 26 |
| 4a phorbol didecanoate 1μM | 187 | 73 | 27 | 170 | 27 | 73 |
| 5-HT 100μM | 175 | 69 | 31 | 188 | 66 | 34 |
| 5-HT 100μM + Spiperone 1μM | 392 | 75 | 25 | 204 | 36 | 64 |

ISO

ISO + PROP

FSK 1,9 DD FSK

PDBu

4α-PDD

FIGURE 9

| DRUG | AVG. # CELLS | % STAINED | % UNSTAINED |
|---|---|---|---|
| CONTROL | 34.00 ± 2.6 | 29.51 ± 3.2 | 70.49 ± 3.2 |
| PDBu | 29.70 ± 2.5 | 75.96 ± 1.7* | 24.04 ± 1.7 |
| 4-ALPHA-PDD | 29.50 ± 1.7 | 25.16 ± 1.3 | 74.84 ± 1.3 |
| ISOPROTERENOL | 26.36 ± 1.9 | 72.93 ± 2.6* | 27.07 ± 2.6 |
| PROPRANOLOL | 30.10 ± 2.2 | 30.31 ± 2.9 | 69.69 ± 2.9 |
| FORSKOLIN | 26.70 ± 1.6 | 65.89 ± 2.5* | 34.11 ± 2.5 |
| 1,9 FORSKOLIN | 28.40 ± 1.4 | 21.65 ± 1.4 | 78.35 ± 1.4 |
| BAFILOMYCIN | 26.30 ± 1.4 | 24.68 ± 2.6 | 75.32 ± 2.2 |

FIGURE 11

|  | CONTROL | TREATED |
|---|---|---|
| VEH/BAF 0.2 | 0.25 ± 0.1 | 0.25 ± 0.1 |
| VEH/BAF 0.4% | 0.25 ± 0.1 | 0.27 ± 0.1 |

METHOD OF TREATING GLAUCOMA WITH OLIGONUCLEOTIDES

Portions of the invention disclosed herein were made with Government support under NIH Grant No. R01-EY-06810 from the Department of Health and Human Services. Accordingly, the U.S. Government has certain rights in this invention.

Throughout this application, various publications are referenced by numbers in brackets. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

One of the mainstays of glaucoma treatment is the use of drugs that decrease the secretion of aqueous humor fluid from the ciliary epithelium. Unfortunately, many currently available drugs that decrease aqueous humor production such as β-adrenergic antagonists, may cause serious systemic side effects such as cardiac arrhythmias, and arrest, pulmonary bronchospasm, and CNS side effects such as decreased libido and depression [13, 40, 66]. Similarly, the systemic use of carbonic anhydrase inhibitors is associated with blood dyscrasias, renal calculi, and mental changes such as confusion and depression, paresthesia of the extremities and electrolyte disturbances [12].

The development of effective aqueous suppressants in patients who are suffering from glaucoma will result in decreased morbidity and mortality in the population. Glaucoma is a complex disease characterized chiefly by an increase in intraocular pressure. If the intraocular pressure is sufficiently high and persistent, it may lead to damage to the optic disc at the juncture of the optic nerve and the retina. The result of high intraocular pressure is irreversible and can cause blindness. There are three types of glaucoma characterized: primary, secondary, and congenital.

The vacuolar $H^+$-ATPase (V-ATPase) resides on the plasma membrane of the ciliary epithelium and acts as an important ion motive force in aqueous humor production. Translocation of this enzyme to and from the plasma membrane appears to be an important mechanism by which aqueous humor production may be regulated.

No model exists to explain the action of carbonic anhydrase inhibitors in the ciliary epithelium in the non-pigmented epithelium (NPE). Immunostaining of the NPE in rabbit ciliary epithelium was identified [9]. As described herein, we disclose that a proton pump belonging to a different class of enzymes, namely the vacuolar $H^+$-ATPases, is present in the basolateral membrane of the non-pigmented and pigmented epithelium (PE) cells of the rabbit ciliary epithelium and in SV-40 transformed human-derived nonpigmented and bovine-derived pigmented ciliary epithelial cells grown in tissue culture.

The V-ATPase pump is recruited to the plasma membrane in the ciliary epithelium and in cultured ciliary epithelial cells by drugs which alter adenylyl cyclase and phospholipase C. Drugs which alter these second messenger systems are thought to be important in the regulation of aqueous humor production [68]. Furthermore, drugs such as propranolol, a β-adrenergic antagonist, inhibited the recruitment of proton ATPase to the plasma membrane.

Most of the membrane organelles in a typical eukaryotic cell belong to the elements of the exocytic and endocytic pathways, referred to collectively as the vacuolar system [37]. They include the endoplasmic reticulum, the golgi complex, the secretory vacuoles, the endosomes, the lysosomes, and other organelles involved in biosynthesis, processing, transport, storage, release, and degradation of soluble and membrane-bound macromolecules. An important similarity among the organelles of the vacuolar system is the presence of $H^+$-ATPases responsible for generating all internal acidic environment.

There are two mechanistically distinct groups of ATP dependent ion pumps. One group, the P-ATPases ($E_1E_2$ ATPases) operate with a phosphoenzyme intermediate and its members (i.e. $Na^+/K^+$ATPase, gastric $H^+$ATPase) are usually sensitive to low concentration of vanadate, a phosphate transition state analog. The P-ATPases are present in the cell membranes of fungi, plants, animals, sarcoplasmic reticulum of muscle cells, and the bacterial cytoplasmic membranes.

The other group, contains the families of $F_1F_0$ ATPases (F-ATPases) and vacuolar $H^+$-ATPases (V-ATPases) [21, 39, 42, 43]. F-ATPases and V-ATPases function without a phosphorylated intermediate, [41] are multisubunit protein complexes that are built of distinct catalytic and membrane sectors, are not sensitive to low vanadate concentrations, but are sensitive to bafilomycin A [5, 70, 77].

The vacuolar proton ATPases are distinguished from the other two classes by virtue of their inhibitor specificities, lack of coupling to counter-ion transport, and intracellular distribution. V-ATPase inhibitors include: N-ethylmaleimide (NEM), 4-chloro-7-nitrobenzo-2 -oxa-1,3-diazole (NBD-Cl) [3, 16, 18, 49, 67] N,N'-dicyclohexylcarbodiimide, Nethymaleimide, $NO_3-$, bafilomycin A [5, 70], concanamycin [77], suramin [38] and fusidic acid [38].

The family of V-ATPases are present in archaebacteria and vacuolar systems of eukaryotic cells. While the family of F-ATPases function in eubacteria and are present exclusively in the thylakoid membrane of chloroplasts, inner mitochondrial membrane and bacterial cytoplasmic membranes.

V-ATPases pump protons without internal counterions and therefore are inherently electrogenic. Since they use ATP, they are also strongly oxygen-dependent in cells with low anaerobic phosphorylating capacity. They energize membranes by transducing the energy from ATP hydrolysis into a proton current, which establishes an electrochemical gradient $\Delta\mu H$.

The vacuolar $H^+$-ATPases are ubiquitous intracellular proton pumps in cells. They serve to acidify intracellular compartments and organelles in mammalian cells such as lysozomes, golgi, and synaptic vesicles and thus lower intralumenal pH. In addition, the vacuolar $H^+$-ATPases may serve to modulate cellular functions in conjunction with its external milieu.

The vacuolar $H^+$-ATPases are all 500 kD–600 kD molecular weight (Mr) proteins with generally at least eight different component subunits. All have subunits of approximately 70 kD, 56 kD, several subunits between 30 and 50 kD, and at least one low molecular weight subunit of 17 kD. In all of the enzymes, most of the large molecular weight proteins are peripheral membrane proteins that do not have any membrane spanning portions, and the small molecular weight proteins are intrinsic membrane proteins that span the lipid bilayer.

The vacuolar $H^+$-ATPases have two major domains, the cytoplasmic domain and the transmembrane domain (FIG.

1). The cytoplasmic domain is the locus of the catalytic and probable regulatory sites of the enzyme, and is composed of peripheral membrane proteins. The transmembrane domain forms the channel through which protons cross the lipid bilayer and is composed of intrinsic membrane proteins which the cytoplasmic domain and anchor it on the membrane.

The cytoplasmic domain contains the ~70 kD ("A") subunit of the vacuolar $H^+$-ATPases and appear to have the site where ATP is hydrolyzed during proton transport. There are 3 subunits of 70 kD in each complete proton pump. Cloning and Southern blotting of this subunit from bovine genomic DNA suggests that there is only one gene for the 73 kD subunit [49]. The sequences of the 70 kD subunit and its homolog have a highly conserved domain in the mid-coding region which comprise the nucleotide binding and catalytic site. The sequence of the bovine kidney subunit compared with the plant and the fungal enzymes show wide divergence at the amino-terminal and carboxyl-terminal domains, with no sequence conservation. It is possible that these regions have a regulatory or non-catalytic role.

There are 3 subunits of 56 kD ("b" subunit) per $H^+$-ATPase. The function of this subunit is uncertain. The subunit is homologous to the αsubunit of the $F_0F_1$ $H^+$-ATPase. The αsubunit does not have a catalytic ATP binding site, but is required for catalytic activity. It has a high affinity nucleotide binding site which is thought to be involved either in regulation of the enzyme, or as a non-hydrolytic part of the reaction mechanism. The function of the 56 kD subunit of the vacuolar $H^+$-ATPases ATPases is unknown although evidence from the plant enzyme suggests that it may have an ATP binding site. Cloning of the subunit has revealed that there are at least two different isoforms of the 56 kD subunit in the kidney, and these are encoded by different genes [44, 50].

Vacuolar $H^+$-ATPase affinity purified from a bovine kidney cortex microsomal fraction had different enzymatic properties from V-ATPase isolated from bovine kidney brush border, in addition to heterogeneity of the 56 kD and 31 kD subunits [67]. The 56 kD subunit therefore has an important role in determining the tissue specific enzymatic properties or compartmentation of the vacuolar $H^+$-ATPase.

There are from 1 to 3 subunits of the 31 kD per $H^+$-ATPase. The cDNA has been cloned from bovine kidney [35]. Monoclonal antibodies raised against heterogeneous 31 kD subunits in the renal brush border and collecting tubules are consistent with preliminary data from immunoscreening genomic DNA that suggests more than 1 gene codes for this subunit [24]. The amino acid sequence of the subunit is 98% identical between different mammalian species, far higher than for the 70 and 56 kD subunits.

The function of the other subunits of the cytosolic domain is not established, but they may constitute a "stalk" domain connecting the catalytic portion to the intrinsic membrane domain similar to the construction of the $F_0F_1$ enzymes.

The transmembrane domain forms a proton conducting channel that spans the lipid bilayer [41]. Although the entire composition of this portion of the enzyme remains in dispute, all of the vacuolar $H^+$-ATPases have an approximately 17 kD (or 15 kD in the kidney) polypeptide that reacts readily with the hydrophobic α-carboxyl reagent dicyclohexylcarbodiimide.

The ciliary epithelium is a double layer epithelium composed of two cell types whose apical ends face each other. Both the outer nonpigmented (NPE) and inner pigmented (PE) epithelial layers exhibit properties of transporting epithelia [23]. The NPE is thought to provide the direct driving force for aqueous humor formation. Physiologic and immunocytochemical evidence suggests that the $Na^+/K^+$-ATPase resides in the basolateral membrane driving sodium secretion and providing the main ion motive force for driving sodium dependent cotransporters [7, 11, 15, 45, 65].

Electroneutrality is thought to be maintained by anion channels in the NPE basolateral membrane. However, the NPE is coupled to the PE through an extensive network of gap junctions and therefore the bilayer is thought to function electrogenically as a syncytium [32, 55, 71, 72]. Solute entry in to dual epithelium is thought to occur at the basolateral surface of the pigmented epithelial cells through several sodium dependent cotransporters ($Na^+$-H exchange, $Na^+$ dependent $NaHCO_3^-$ exchange, electroneutral $Na^+Cl^-$ cotransport and others) [6, 73, 76].

SUMMARY OF THE INVENTION

The present invention provides a method of treating glaucoma, which comprises administering to a subject an effective amount of an oligonucleotide which may be substituted or modified in its phosphate, sugar, or base, so as to decrease intraocular pressure and thereby treat the glaucoma.

Figure 1:
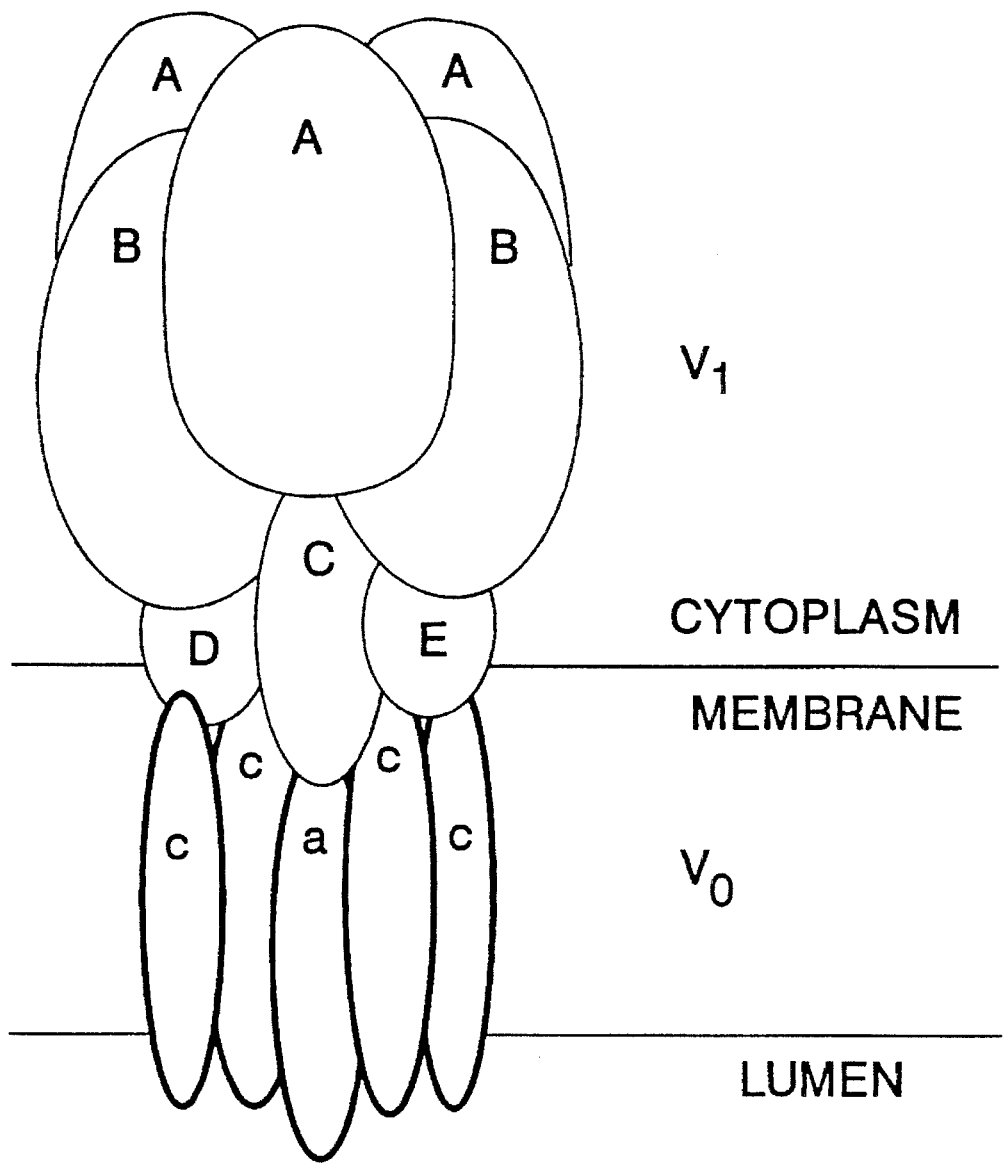
FIG. 1.

V-ATPase subunit structure drawn according to the enzyme of chromaffin granules. The molecular weights of subunits A,B,C,D,E,a, and c are 70 kD, 57 kD, 44 kD, 30 kD, 26 kD, 20 kD, and 16 kD, respectfully.

FIG. 2:

Western blot of rabbit tissue: Freshly dissected rabbit tissues: (Br) liv (LIV) kidney (Kid) and ciliary body (CB), were lysed in hypotonic buffer, homogenized, and centrifhged at 1000XG to remove nuclear material. SDS-PAGE was performed on the remaining homogenate and the antibody to the "renal"56kD subunit of proton ATPase was used as the primary antibody.

FIG. 3A–FIG. 3B:

Immunocytochemistry of the rabbit ciliary process. Semithin 1 μM sections were cut from tissue embedded in LX-112 and were treated with a mixture of KOH, propylene oxide and methanol to remove the resin. Sections are incubated in PBS containing 1% bovine serum albumin to reduce non-specific background staining and then with a rabbit polyclonal antibody to the 56 kD subunit ("kidney form") of vacuolar proton-ATPase. Fluorescein isothiocyanate-labeled goat anti-rabbit immunoglobin was used as the secondary antibody. The sections were mounted in 50% glycerol/PBS and photographed with an epifluorescent microscope. Preimmune sera failed to reveal any significant staining.

FIG. 4A–FIG. 4D:

Immunocytochemistry of rabbit ciliary epithelium following drug treatment. Rabbit iris/ciliary bodies (I/CB) are freshly dissected and sectioned into 6 pieces per I/CB ring, and maintained in modified oxygenated Krebs buffer for 30 minutes in which buffer is changed twice. The tissue is then treated for 20 minutes with 100 μM isoproterenol in the absence and presence of propranolol (1 μM). Ciliary body sections were embedded in EPON and 1 μM semithin sections were stained with a polyclonal antibody to the 56kDsubunit of vacuolar proton ATPase as described.

FIG. 5A–FIG. 5D:

Rabbit ciliary epithelium treated with phorbol esters. Freshly dissected ciliary processes were treated with 1 µM of active phorbol ester phorbol 12, 13 dibutyrate (PDBu), or the inactive phorbol ester didecanoate (4αPDD) and prepared for immunocytochemistry as described.

FIG. 6:

Immunoreactivity in response to drugs in the ciliary processes.

FIG. 7A–FIG. 7C:

In control NPE cells, proton ATPase was distributed in vacuoles throughout the cytoplasm. Staining with pre-immune sera and peptide competition was negative.

FIG. 8A–FIG. 8F:

In response to 100 µM isoproterenol (ISO), 10 µM forskolin (FSK) or 1 µM phorbol ester 12, 13 dibutyrate (PDB) the appearance of the enzyme on the plasma membrane was observed. Coincubation of ISO with 1 µM propranolol (PROP), inactive forskolin 1, 9 didecanoate (1, 9 DD FSK) and inactive phorbol (1α-PDD) failed to demonstrate the presence of membrane staining of the 56kD proton ATPase subunit.

FIG. 9:

Evidence that the NPE from an Origin Defective Mutant ($ODM_2$) cell line may serve as an effective model in which to study vacuolar $H^+$-ATPase. The number of positive-staining cells per field is quantitated in response to drugs (n=10). The significant changes (*=p<0.5) that occur in response to isoproterenol, forskolin and phorbol ester mimic those changes that occur in the intact rabbit ciliary epithelium crypt.

FIG. 10A–FIG. 10C:

Rabbits (n=3) were given 50 µl of bafilomycin (BAF or DMSO vehicle (VEH). Intraocular pressures (IOP) were recorded for 6 hours and reported as differences from baseline values (approximately 24 mm Hg). The IOP's in the treated eyes were significantly different from control eyes (*=p<0.5) at 1 hr for 0.2% and 0.4% bafilomycin. (Different rabbits were used for each concentration).

FIG. 11:

Outflow facility (Co) in µl/min/mm Hg following topical vehicle (DMSO) or bafilomycin (BAF).

FIG. 12A–FIG. 12B:

IOP in rabbits following a single 50 µl topical dose of water vehicle (VEH) or drug (n=3) (*p=<0.5). A single topical application of SDC28 resulted in a dose dependent lowering of rabbit IOP in comparison to control eyes. The maximal effect was short action (peak 1–2 hrs), but of significant magnitude.

DETAILED DESCRIPTION OF THE INVENTION

The present invention provides a method of treating glaucoma which comprises administering to a subject an effective amount of an oligonucleotide which may be substituted or modified in its phosphate, sugar, or base, so as to decrease intraocular pressure and thereby treat the glaucoma. Further, aqueous humor formation in an eye may be decreased or aqueous outflow from the eye may be facilitated in order to treat the glaucoma.

Oligonucleotides are compounds made up of repeating units of nucleotides. The oligonucleotide may be substituted or modified in its phosphate, sugar, or base. These compounds are also known as chimeric oligonucleotides.

Synthetic oligodeoxynucleotides have been utilized as antisense inhibitors of mRNA translation in vitro and in vivo [26, 51, 64]. Antisense oligonucleotides have found widespread application because of their abilities to control and/or inhibit gene expression in a selective manner in cellular systems [15, 34, 54, 63, 82]. Phosphorothioate oligodeoxynucleotides are relatively nuclease resistant water soluble analogs of phosphodiester oligodeoxynucleotides. These molecules are chiral but still hybridize well to their RNA targets [57].

Further, since many classes of oligodeoxynucleotides (e.g., phosphodiesters (PO) and phosphorothioates (PS)) are polyanions, they cannot passively diffuse through lipophilic cell membranes [58]. However, the majority of oligonucleotide internalization is not due to receptor-mediated endocytosis, but rather results indicate that bulk internalization is predominantly from pinocytosis, fluid-phase endocytosis.

Throughout this application, references to specific nucleotides are to nucleotide present on the coding strand of the nucleic acid. The following standard abbreviations are used throughout the specification to indicate specific nucleotides:

C=Cytidine
T=Thymidine
A=Adenosine
G=Guanosine

The oligonucleotide may be an oligodeoxynucleotide, a phosphorothioate, a phosphorodithioate, a chimeric oligonucleotide, an oligonucleotide homopolymer, or an oligonucleotide heteropolymer. In one embodiment the oligonucleotide is a chain of cytidine nucleotide sequences. In another embodiment the oligonucleotide is a chain of adenosine nucleotide sequences. In another embodiment the oligonucleotide is a chain of guanosine nucleotide sequences. In another embodiment, the oligonucleotide is a chain of thymidine nucleotide sequences. The most preferred embodiment is the cytidine nucleotide sequence. The oligonucleotide sequence may be in either a stereo regular or stereo non-regular configuration.

A homopolymer is a sequence of repeating cytidine, guanosine, adenosine, or thymidine nucleotides or other natural bases thereof. For example, SdC28 is a phosphorothioate oligonucleotide that is a homopolymer of cytidine for a 28 base length sequence. A heteropolymer is a sequence of alternating cytidine, guanosine, adenosine, or thymidine nucleotides, or natural bases thereof. For example, SdCT20 is a phosphorothioate oligonucleotide that is heteropolymer of cytidine and thymidine for a 20 base length sequence.

In one embodiment the oligonucleotide sequence is a short chain structure, 5–20 nucleotides. In another embodiment the oligonucleotide sequence is a long chain structure, 20–100 nucleotides. The most preferred structure is a long chain 24 oligonucleotide structure.

The present invention further claims a method of treating glaucoma in a subject which comprises, administering to the subject an effective amount of phosphorothioate so as to thereby treat the glaucoma. Phosphorothioate may be in either a stereo regular or stereo non-regular configuration.

The phosphorothioate may further be linked to a 3' or 5' -cholesteryl moiety. Alternatively, the phosphorothioate may be modified in the bridge wherein the one of the two oxygen atoms involved in the bridge are replaced with analogues such as NH—, $CH_2$— or S—.

Phosphorothioate (PS) is an oligodeoxynucleotide in which the sulfur atom replaces one of the non-bridging oxygen atoms at each interbase phosphorus atom. The phosphorothioate can occur at each PS linkage either as Rp or Sp diastereomers. Because of phosphorothioate's nuclease resistant properties it is an effective inhibitor of replication of Human Immunodeficiency Virus (HIV-1) in cell culture [1, 2, 36]. PS oligonucleotides are non-sequence specific and act as inhibitors of the HIV-1 cytopathic effect in de novo infected ATH8 cells. With Sd(GGC)9, maximal cytoprotection was observed at a concentration of 0.3 μM. In a series of A-T rich PS oligomers, including SdA21, SdT21, SdCT20 and SdCT19C, all, with the exception of SdA21, were of approximately equal potency. The same generalization was true in a series of non-homopolymeric PS oligomers, including the self-complementary S-d(CG)10G, S-d(GGC)7, S-d(C5T)3C3, S-d(CCT)7, s-d(CCA)7, S-d(CT)10C, S-d(CTT)7 and S-d(GTT)7. Indeed, the inhibitory effect was entirely independent of the base sequence, though for a 14 base length oligonucleotide, it was more pronounced with PS oligomers of increasing GC content, even with the phosphoroselenoate oligomer S-dC28 [1, 2].

This invention further claims the oligonucleotide which may be substituted or modified in its internucleotide phosphate residue with a thioether, carbamate, carbonate, acetamidate or carboxymethyl ester.

In addition, the oligonucleotide may be substituted or modified in its sugar with a ribose, 2' allyl, glucose, sucrose, or galactose or any other sugar. Alternatively, the oligonucleotide may be substituted or modified in its 2' position; such as 2'-O-methylribonucleotide. Further, the oligonucleotide may be substituted or modified to form an α-anomeric sugar.

In addition, the oligonucleotide may be substituted or modified in its base. Apart from the bases of adenine, guanine, cytosine, and thymine, other natural bases such as inosine, deoxyinosine, hypoxanthine are acceptable. In addition, isosteric purine 2' deoxy-furanoside analogues, 2'-deoxynebularine or 2' deoxyxanthosine, or other purine or pyrimidine analogues may also be used.

The present invention further provides that a 5' end of the oligonucleotide may be linked with: intercalating agents, such as acridine derivatives; cross-linkers, such as psoralen derivatives, azidophenacyl, proflavin, and azidoproflavin; artificial endonucleases, which comprise those conjugates whose nuclease component is able as such to cleave DNA specifically and nonspecifically, and acquires a specificity by covalent linkage to the oligonucleotide, such as metal complexes EDTA-Fe(II), o-phenanthroiine-Cu(I), and porphyrinFe(II); and lipophilic carriers or peptide conjugates, such as long chain alcohols as phosphate esters, amino or mercapto groups, dyes or nonradioactive markers and polysine.

The present invention further provides that a 3' end of the oligonucleotide may be linked with: intercalating agents, such as 2 -methoxy- 6 - chloroacridine, methylphosphonates, methylesters, and aminoalkyls; alkylating oligonucleotides, such as acetyl; artificial endonucleases, such as amino- 1 -hexanolstaphylococcal nuclease, and alkaline phosphatase; peptide conjugates, such as polylysine; and terminal transferases.

The oligonucleotides in the present invention may be conjugated to a carbohydrate, sulfated carbohydrate, or glycan. Conjugates may be regarded in such a way as to introduce a specificity into otherwise unspecific DNA binding molecules by covalently linking them to a selectively hybridizing oligonucleotide.

The type of glaucoma includes, but is not limited to: acute glaucoma, absolute glaucoma, chronic glaucoma, congenital glaucoma, juvenile glaucoma, narrow angle glaucoma, open angle glaucoma, and simplex glaucoma.

The oligonucleotide may be in combinations with other antiglaucoma therapies such as: Acetazolamide, Befundolol, Betaxolol, Bupranolol, Carteolol, Dapiprazole, Dichlorphenamide, Dipivefrin, Epinephrine, Levobunolol, Matheazolamide, Metipranolol, Pilocarpine, Pindolol, and Timolol.

An "effective amount" as used herein refers to that amount of oligonucleotide which decreases intraocular pressure in a subject. The effective amount may be in the range of 1 nM to 10 mM.

Carriers for topical administration include: aqueous vehicles containing additional ionic buffers as required for pharmacokinetic efficacy, glycerol, mannitol, peanut oil, and sesame oil, surfactants such as polyvinylalchohol or any other additional substrates which would promote tear film-cornea contact time, and other vehicles which are known to one of ordinary skill in the art.

For topical administration, the preferable administration is in a dosage range of 0.1 mM to 0.5 mM.

Further, as is known to those of ordinary skill in the art effective amounts vary with the type of therapeutic agent. It is known to those of ordinary skill in the art how to determine an effective amount of a suitable therapeutic agent.

The subject may be a mammal or more specifically a human, horse, pig, rabbit, dog, monkey, or rodent.

As used herein administration means a method of administering to a subject. Such methods are well known to those skilled in the art. and include but are not limited to administration topically, parenterally, orally, intravenously, intramuscularly or subcutaneously. Administration of the agent may be effected continuously or intermittently such that the therapeutic agent in the patient is effective to decrease intraocular pressure.

Further, the most preferred method of administration is by topical administration of a solution into the eye of a subject.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

EXPERIMENT 1

The 56kD subunit of vacuolar proton-ATPase is present in the ciliary epithelium.

Figure 2:
Figure 3A:
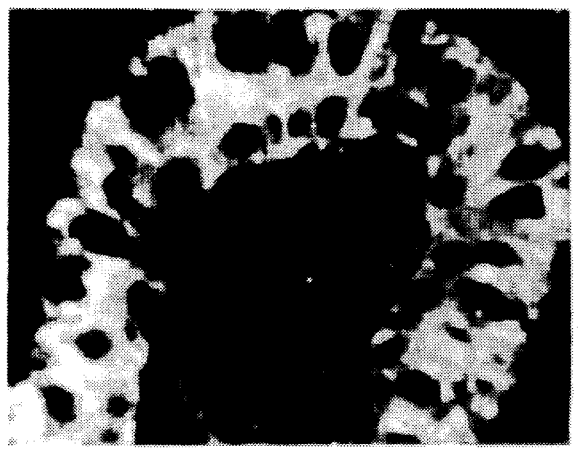
Figure 3B:
Figure 4A:
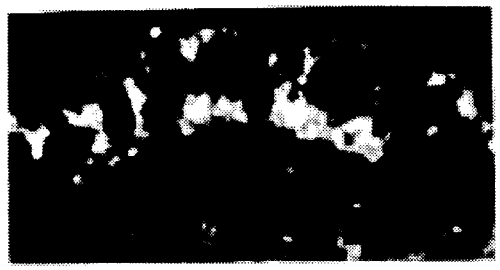
Figure 4B:
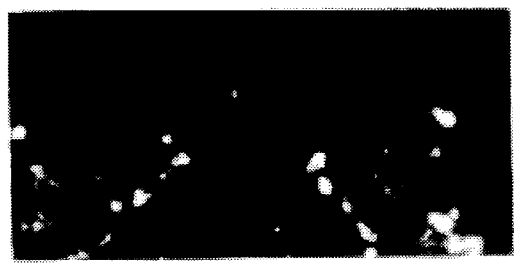
Figure 4C:
Figure 4D:
Figure 5A:
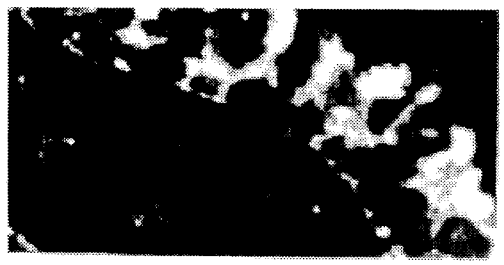
Figure 5B:
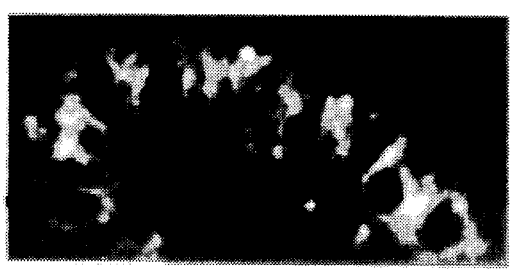
Figure 5C:
Figure 5D:

Immunocytochemical techniques and immunoblotting, has identified the presence of vacuolar $H^+$-ATPase in the rabbit ciliary epithelium. Immunostaining of the intact rabbit ciliary epithelium was employed with antibodies that have been successfully used to identify selective "renal" and "brain" specific isoforms of the 56kD subunit of vacuolar $H^+$-ATPase [44]. Immunoreactivity was identified in both ciliary epithelial bilayers for only the "renal" isoform of vacuolar $H^+$-ATPase (FIG. 3A–FIG. 3B). Using the same "renal" specific antibody, a Western blot confirmed the presence of the 56kD subunit in the rabbit ciliary epithelium (FIG. 2). A band was identified in the ciliary epithelium and rabbit kidney, but not from brain or liver. These results extend the presence of a tissue specific 56kD subunit of vacuolar $H^+$-ATPase to the ciliary epithelium.

The identification of the 56kD subunit of vacuolar $H^+$-ATPase in the ciliary epithelium is significant for two reasons. First, although vacuolar ATPase is a ubiquitous intracellular enzyme in all eukaryotic cells, the appearance of vacuolar ATPase in the plasma membrane of both epithelial bilayers of the ciliary epithelium was unexpected. This observation has been previously reported in only a few known cell types such as the intercalated cell of the kidney and bone osteoclasts. In kidney and bone, the appearance of a membrane form of vacuolar $H^+$-ATPase is associated with a critical function of proton secretion. In the osteoclast, proton secretion is thought to be essential for bone resorption, and in the collecting duct of the kidney, the specialized proton pump of the intercalated cell is thought to be important for bicarbonate resorption from urine [79]. In the eye, membrane bound $H^+$-ATPase is important in bicarbonate transport in the ciliary epithelium. Secondly, although staining is mainly observed in the basolateral surfaces of the nonpigmented and pigmented ciliary epithelia, there is a clear distributional difference in positive staining in regions of the ciliary process tip versus those of the ciliary process crypt. In the tip, the appearance of the 56 kD subunit in the mostly basolateral domain appears in both the NPE and PE, however, in the crypt, NPE staining is minimal or absent, and staining is mostly confined to the basolateral domain PE layer.

EXPERIMENT 2

Drugs cause translocation of vacuolar proton ATPase from the cytoplasm to the membranes in the rabbit ciliary epithelium and redistribution of the enzyme in the ciliary processes.

Experiments were performed to study whether or not the appearance of the membrane bound form of vacuolar $H^+$-ATPase in the ciliary epithelium is regulated by drugs known to affect aqueous humor production such as those which activate cAMP dependent protein kinase and protein kinase C. In eyes treated with isoproterenol the distribution of the membrane bound $H^+$-ATPase was markedly altered most dramatically in the NPE layer (FIG. 4A–FIG. 4D). In response to 100 μM isoproterenol, staining in the NPE layer in the ciliary process tip was more pronounced in the apical domain, and NPE staining was also clearly heavily present in the ciliary process crypt. Both of these changes were blocked by the coincubation of propranolol (1 μM) with isoproterenol during tissue treatment. Similarly, freshly dissected ciliary processes treated with 1 μM phorbol ester (phorbol 12, 13 dibutyrate) resulted in the dramatic appearance (FIG. 5A–D) of the nonpigmented epithelial staining in the ciliary process crypts, in addition to increased apical staining in the tip region. These alterations were not observed with the use of inactive phorbol didecanoate (4α-didecanoate). These observations suggest that translocation and/or redistribution of proton ATPase is a mechanism integral to the production and regulation of aqueous humor. In addition, to our knowledge, the translocation of vacuolar $H^+$-ATPase in response to drugs which activate protein kinase A and C is previously unreported in any tissue.

The appearance of cells which manifest positive immunoreactivity in response to drugs, is not completely uniform throughout the ciliary processes. The number of positive membrane-staining cells present in ciliary epithelial tips or crypts was quantitated as an alternate method of demonstrating the effect of drugs in redistributing the immunoreactivity of the 56kD subunit, particularly to the crypts, in the ciliary processes. Since microtome sectioning of the tissue yielded ciliary processes that were of different lengths, the total number of stained or unstained cells in an average of 8–10 processes were recorded. The results are summarized in FIG. 6.

EXPERIMENT 3

The 56kD subunit of vacuolar proton ATPase is present in human-derived, SV-40 transformed nonpigmented ciliary epithelia cells.

Figures 7A, 7B, 7C:
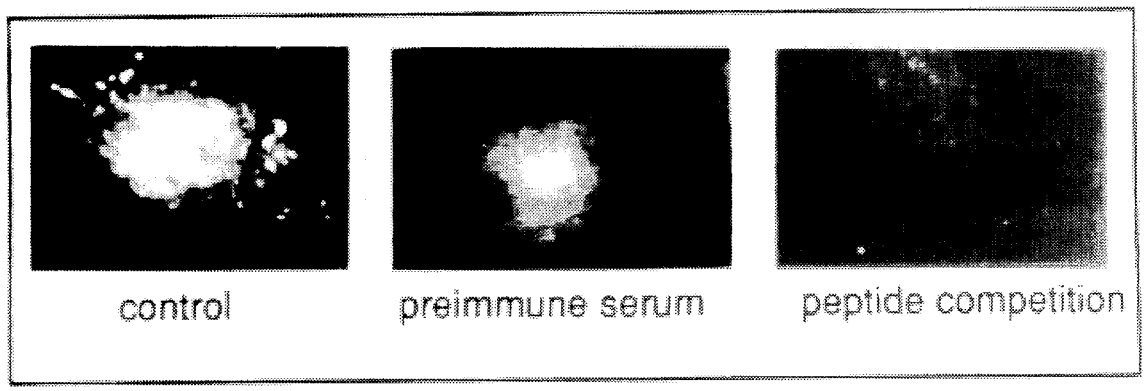
Figure 8A:
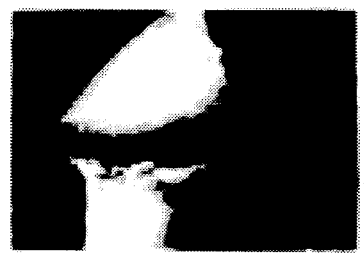
Figure 8B:
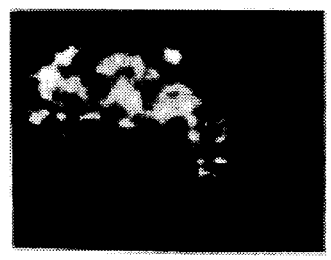
Figure 8C:
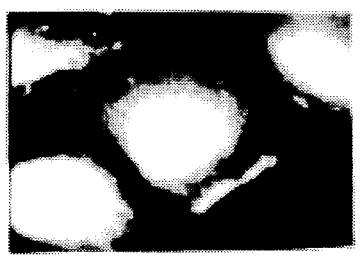
Figure 8D:
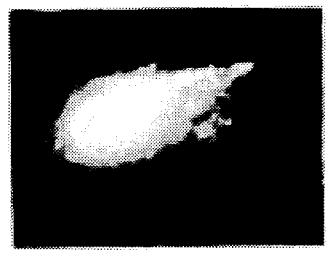
Figure 8E:
Figure 8F:
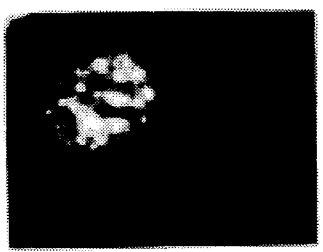

In order to assess whether a cell culture model to study the cellular basis of these effects could be developed, the effects of isoproterenoi or phorbol ester treatment on the translocation or redistribution of proton ATPase in SV-40 transformed human-derived NPE and bovine PE cells was examined. These cells have been widely used and are useful for the study of ciliary epithelium since they retain many electrophysiological and pharmacological properties of the native tissue [68]. In control NPE cells (FIG. 7A–FIG. 7C) proton ATPase was distributed in vacuoles throughout the cytoplasm. In response to 100 μM isoproterenol (ISO), 10 μM forskolin (FSK) or 1 μM phorbol ester 12, 13 dibutyrate (PDB) the appearance of the enzyme on the plasma membrane was observed (FIG. 8A–FIG. 8F). However, the coincubation of ISO with 1 μM propranolol (PROP), inactive forskolin 1, 9 didecanoate (1, 9 DD FSK) and inactive phorbol (1α-PDD) failed to demonstrate the presence of membrane staining of the 56 kD proton ATPase subunit (FIG. 8).

Thus, the clone ($ODM_2$) of human-derived nonpigmented cells in culture appears to be an effective cell model in which to the study the mechanism of the plasma membrane vacuolar $H^+$ATPase translocation that occurs in vivo in response to drugs. This proton pump is coupled to the movement of several ions, such as bicarbonate, across the highly selective epithelial component of the blood eye barrier. The identification of this proton pump in the ciliary epithelium now permits further investigation of its functional role in the physiology of this secretory epithelium and may provide a new target for pharmacologic manipulation of aqueous production and transport. Further evidence that the NPE ($ODM_2$) cell line may serve as an effective model in which to study vacuolar H+ATPase can be found in FIG. 9, in which the number of positive-staining cells per field is quantitated in response to drugs (n=10). The significant changes (*=p<0.5) that occur in response to isoproterenol, forskolin and phorbol ester mimic those changes that occur in the intact rabbit ciliary epithelium crypt.

EXPERIMENT 4

Inhibitors of vacuolar $H^+$-ATPase lower intraocular pressure following topical application.

Figure 10A:
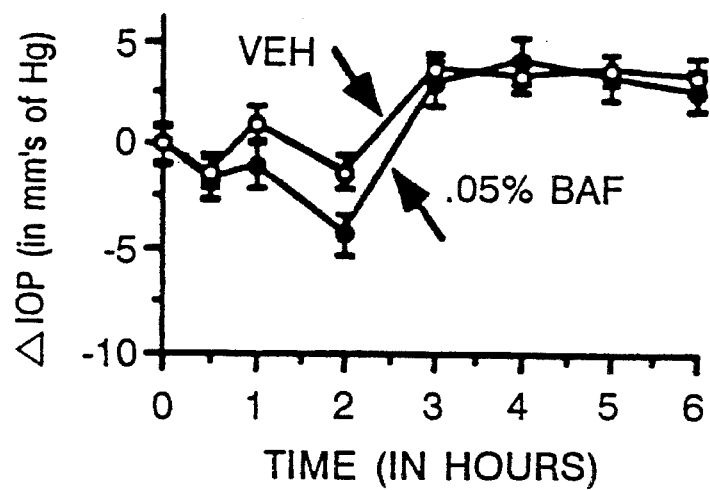
Figure 10B:
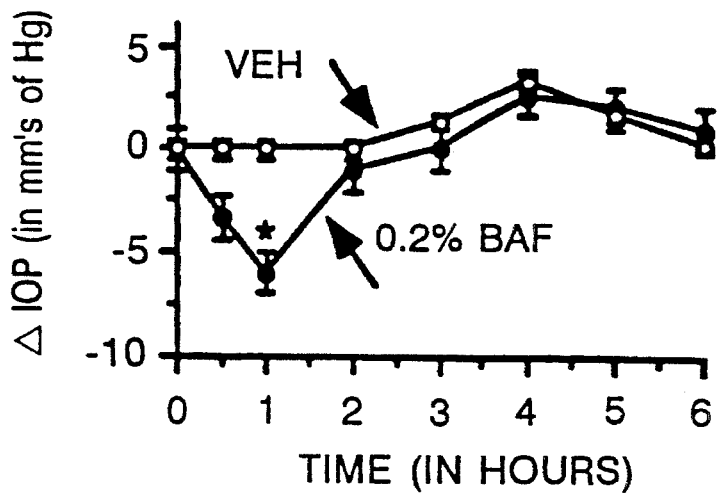
Figure 10C:
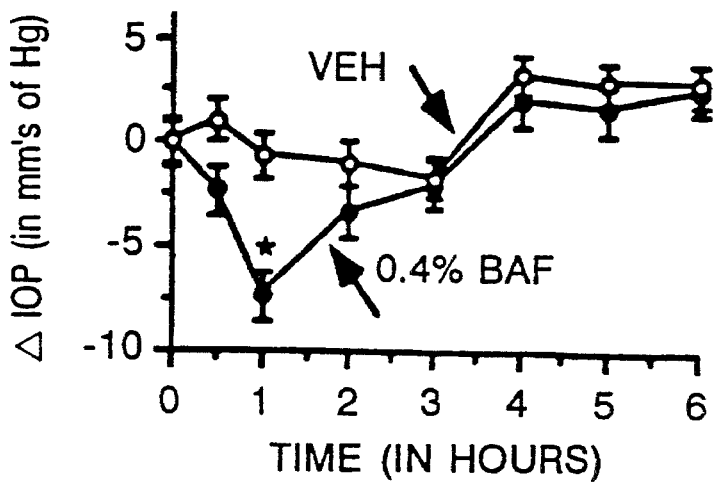

Membrane bound vacuole $H^+$-ATPase is present in the ciliary epithelium, and any assumptions about the potential importance of this enzyme in the regulation of IOP would be premature unless a direct connection between enzyme activity and IOP could be established. Bafilomycin, a specific inhibitor of vacuolar $H^+$-ATPase [79], was ascertained as to whether it lowers IOP in rabbits. The data indicated that the topical application of bafilomycin $A_l$, in fact, lowers IOP in a dose-dependent manner (FIG. 10A–FIG. 10C).

To assess whether the ocular hypotensive effect of bafilomycin is due to reduced aqueous inflow, or to enhanced outflow facility, tonography on rabbits 1 hour following treatment with either 0.2% or 0.4% bafilomycin (n=3) was performed. These results, summarized in FIG. 11, indicate that there are no effects on outflow that result from bafilomycin treatment. These results suggest that the inhibition of vacuolar $H^+$-ATPase in the ciliary epithelium results in decreased aqueous production as the mechanism which underlies the observed ocular hypotensive effects.

EXPERIMENT 5

Oligonucleotides lower intraocular pressure in rabbits.

Figure 12A:
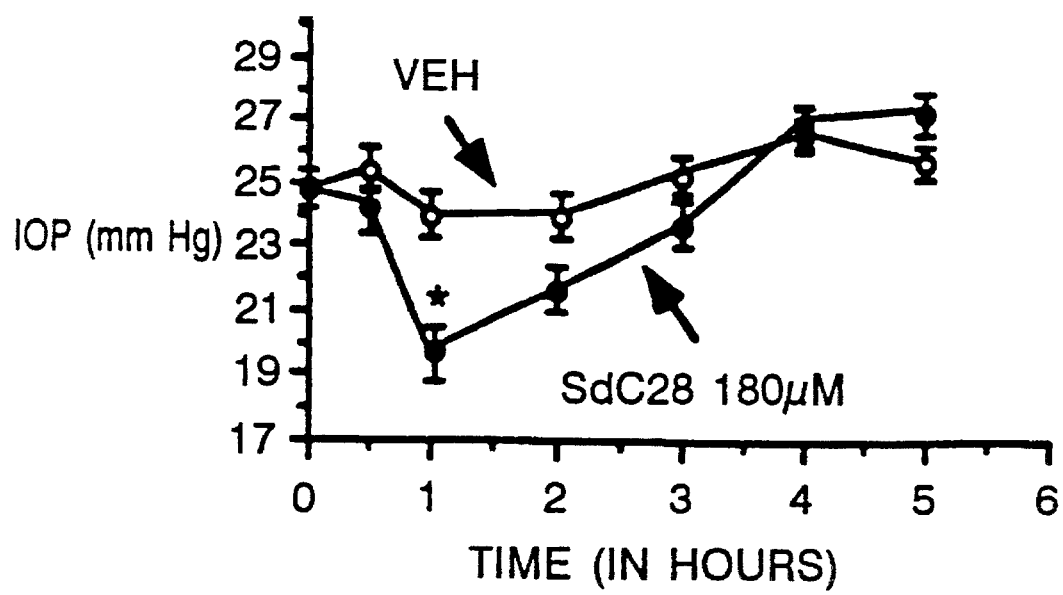
Figure 12B:
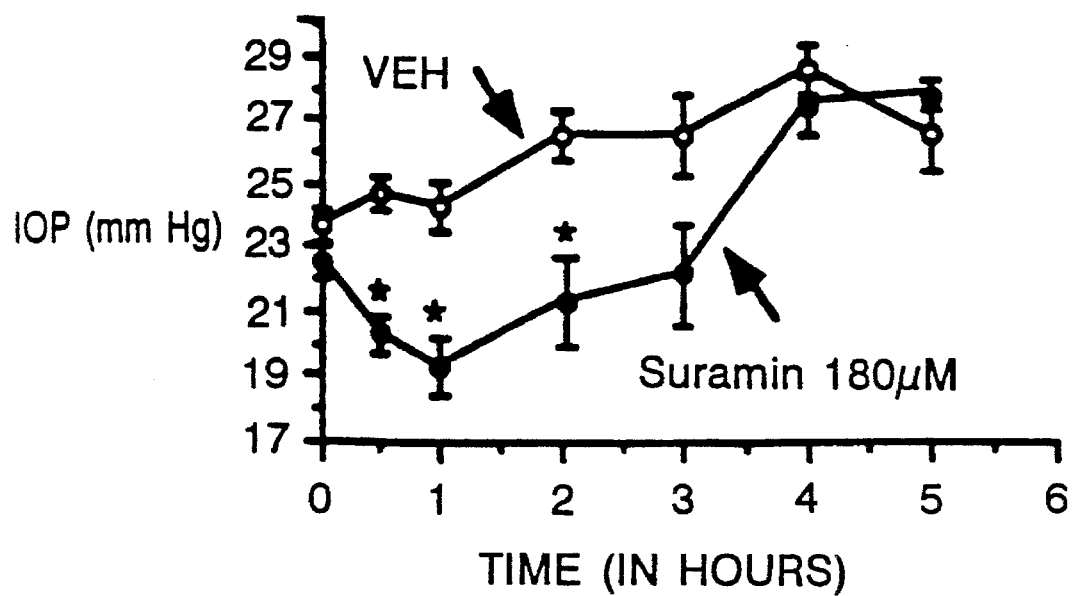

A member of the oligonucleotide family, namely SDC28 (a phosphorothioate oligomer that is a homopolymer of cytidine, 28 bases in length) and suramin were tested for their ability to lower rabbit IOP following topical application. A single topical application of SdC28 and suramin resulted in a dose dependent lowering of rabbit IOP in comparison to control eyes (FIG. 12A–FIG. 12B). The maximal effect was short action (peak 1–2 hrs), but of significant magnitude to have clinical usefulness as antiglaucoma agents.

EXPERIMENT 6

The role of vacuolar $H^+$-ATPase on water and ion transport by the ciliary epithelium.

The data indicates that topical application of SDC28 oligonucleotide results in lowering of rabbit intraocular pressure (IOP). These results indicate that ciliary epithelial vacuolar $H^+$-ATPase is a primary ion motive force in the ciliary epithelium and that the study of inhibitors of this enzyme is useful in developing new treatments for glaucoma. Initial experiments therefore proceed to quantitate the dose dependent effects of oligonucleotides on aqueous humor inflow and outflow.

1. Fluorophotometry:

Bafilomycin is used as a stable solution in DMSO buffer. Concentrations to be tested for their effect on aqueous humor dynamics range from 0.1% to 0.5%. The vehicle is used in the opposite eye as a control. Oligonucletoides are utilized in experiments to assess the effective concentrations of these drugs is performed prior to fluorophotometry experiments. The oligonucleotides range in chain length from 18 to 28 nucleotides, and consist of several backbone modifications including mono and dithioates, phosphorodiesters, and cholestryl moieties.

Albino rabbits weighing 1.8 to 2.5 kg are used for these studies. The rabbits are housed in a daily 12 hour/12 hour light-dark environment to maintain their normal circadian rhythm.

2. Aqueous flow determination:

The rate of aqueous flow is determined using a standard corneal depot fluorophotometric technique [14]. Fluorescence is measured using a Fluorotron Master (Coherent). Twelve hours before measurement of aqueous flow begins, two drops of 10% sodium fluorescein solution (Fundescein; Cooper Vision Pharmaceuticals, Carolina, Puerto Rico) is instilled twice in each eye of the rabbit. Fluorescein concentration is measured in the cornea and in the anterior chamber on an hourly basis for 10 hours starting 12 hours after instillation of the fluorescein solution. Two hours after beginning fluorophotometric readings, 50 ul of one concentration of drug is instilled into the cul-de-sac of one eye while the vehicle is applied to the opposite eye. The aqueous flow rate is determined according to the method of Jones and Maurice [27] and Gaul and Brubaker [14] assuming a 10% clearance of fluorescein by diffusion and a 90% clearance by flow. In the event that aqueous flow rates measured by the above technique are ambiguous, the possibility of interference of topical drug application with corneal fluorescein measurements is ruled out by adminietering the fluorescein isothiocyanate-conjugated (FITC) dextran intravitreally [27]. In this manner, an independent derelimination of aqueous flow is obtained.

3. Tonography:

Outflow facility is studied by tonography, which is performed by measuring intraocular pressure with a Schiotz tonometer every 15 seconds for a total of 2 minutes with topical proparacaine anesthesia. Using these measurements, standard tonographic tables are used to calculate the outflow facility. The outflow facility measurements are performed immediately before topical application of drugs and then 1 hour after application of the drug solution to the eye.

EXPERIMENT 7

The effects of vacuolar $H^+$-ATPase inhibitors on ion flux and intracellar pH in the intact ciliary epithelium and in ciliary epithelial cells.

1. Transepithelial measurements of isolated, intact iris-ciliary body:

Aqueous humor, produced by net fluid movement across the epithelial layers of the ciliary processes, is indirectly assessed by the use of isolated iris-ciliary body preparations in Ussing-Zerahn chambers. Transepithelial measurements performed on the isolated iris-ciliary body (ICB) allows the study of ciliary epithelial transport independent of systemic, local metabolic, circulatory, or neurologic activity. Changes in the short circuit current across the isolated ICB allows the assessment of net solute transport, although changes in SCC do not permit identification of solute transfer in each of the ciliary bilayers individually. Experiments are performed to evaluate net ion transport in iris/ciliary body in response to oligonucleotides. Oligonucleotides inhibit solute transport and therefore decrease the short circuit current in a dose-dependent manner. Examination of transport in cultured cells is not readily performed in an Ussing chamber since it is difficult to grow a monolayer that retains high transepithelial resistance. The results of these experiments confirm that vacuole $H^+$-ATPase is a primary ion motive force in the intact rabbit ciliary epithelium.

Transepithelial electrical measurements are performed as previously described [31]. Dose-response measurements with increasing concentrations of oligonucleotides are obtained by adding these drugs to the aqueous side, blood side or to both sides of the Ussing chamber. Statistical analysis utilizes the Student's t-test on paired differences to compare results within an individual drug experiment. Drug effects are reported as the mean change ±SEM and p values less than 0.05 are considered significant.

2. Measurement of intracellular pH in ciliary epithelial cells and isolated ciliary epithelium:

The role of vacuolar $H^+$-ATPase is best understood in the kidney, where the membrane bound enzyme in intercalated cells of the collecting tubule may facilitate either the reabsorption of bicarbonate and secretion of protons, or the secretion of bicarbonate and reabsorption of chloride. These effects appear to be confined to different subpopulations of intercalated cells that have membrane vacuolar $H^+$-ATPase also serves as a pH regulator in specialized renal cells. In the eye, it has been proposed that bicarbonate transport -is distinctly different in the ciliary epithelial bilayers [75], although the underlying mechanisms are not yet clear. These differences are due to differences of either the intracellular or regional redistribution of the vacuolar $H^+$-ATPase observed in the bilayers of ciliary epithelium in response to drugs. The vacuolar $H^+$-ATPase, in the ciliary epithelium, thus is demonstarted to be an active regulator of ion transport by experiments which assess $H^+$-ATPase specific effects on ciliary epithelial intracellular pH due to alterations in bicarbonate transport.

Microscope-based fluorophotometry was utilized in conjunction with a cell-entrappable pH-reporting dye (BCECF)

to identify and characterize ion-linked bicarbonate transporting systems in ciliary epithelia cells in culture and in freshly dissociated ciliary epithelial preparations. A dual-channel flurophotometer was utilized to assess calcium mobilization in ciliary epithelial monolayers [33] and have adapted this device to a Nikon diaphot microscope to assess fluorescence in single cells. Similar instrumentation has been successfully utilized to study pH in the isolated ciliary epithelial [73–75]. Briefly, ciliary epithelial cells in culture or freshly dissected monolayers is incubated in the 25 µM of the acetoxymethy (AM) form of the fluorescent probe, BCECF. Cells or tissue are maintained in oxygenated, modified Ringers' buffer until use. Excitation with rapidly alternating monochromatic light of 490 and 440 nM is used with emissions at wavelengths greater than 525 nM and excitation rationing, in conjunction with high K+ and nigericin calibration [61] to calculate intracellular pH. Experiments are performed to assess the effects of the specific vacuolar $H^+$-ATPase inhibitor, bafilomycin, on the previously reported decrease of intracellular pH resulting from bicarbonate introduction, or stilbene-sensitive, chloride removal from the media [74], that occurs in the NPE. (These effects appear opposite from those reported for renal intercalated cells in which decreased plasma bicarbonate lowers intracellular pH) [22]. The effects of bafilomycin on pH were examined in response to intracellular acidification (with ammonium chloride treatment) and alkalinization (induced by chloride removal from the media, or by altering bicarbonate concentration in the media). Amiloride is used to eliminate the possible effects on pH due to the presence of the $Na^+/H+$ antiporter. The effects of bafilomycin-sensitive alterations in pH in response to drugs is assessed.

EXPERIMENT 9

The regulation of vacuolar $H^+$-ATPase activity in the ciliary epithelium and in ciliary epithelial cells.

Drugs which alter intraocular pressure may do so by effecting the level of expressed vacuolar $H^+$-ATPase in the ciliary epithelium, or by interfering with a regulatory mechanism in which translocation of the enzyme is altered. For example, topical isoproterenol has been shown to cause an initial increase in aqueous humor production in rabbits [62], and it was demonstrated that within 30 minutes isoproterenol (and forskolin) results in redistribution of the 56kD subunit of the vacuolar $H^+$-ATPase from basolateral domain to an apical domain in many NPE cells of the ciliary tip, and from essentially being absent in the NPE layer in the ciliary crypt, to being quite prominent in the basolateral domain. Although there is no evidence that the production of aqueous is different in ciliary epithelial tips and crypts, alterations in vacuolar $H^+$-ATPase levels, or in cellular redistribution are associated with the altered transport of ions such as bicarbonate. Quantitative immunoblotting was perfomed in cytosol and membrane fractions of ciliary processes and cultured cells in order to assess the levels of vacuolar $H^+$-ATPase subunits in these subcellular fractions. Utilizing monoclonal and polyclonal antibodies to several subunits the relative changes in vacuolar $H^+$-ATPase in each fraction in response to drugs was assesed.

1. Drugs:
In addition to isoproterenol and phorbol esters, changes in cytoplasmic and membrane bound vacuolar $H^+$-ATPase subunits was quantitated in response to a variety of drugs known to alter aqueous production such as beta adrenergic antagonists, atrial natriuretic peptides (which activate guanylyl cyclase), carbonic anhydrase inhibitors, and $alpha_2$ adrenergic agonist such as paraaminoclonidine. When possible, the concentrations of the drugs used are based on their kD's (at the appropriate receptors, obtained from the literature), or on their effective concentrations which lower IOP. When possible, agonist are used with their appropriate antagonists as control. In some cases, inactive species of drugs are used (i.e.4αdidecanoate for phorbol esters, or inactive forskolin) when no antagonist is available. Conditions which result in acidification and alkalinization of the tissues are also studied by treatment with ammonium chloride or sodium bicarbonate.

2. Tissue considerations: The isolation of the intact ciliary body is easily performed, and the ciliary epithelium comprises about 5–10% of the total ciliary body protein. Two methods for the isolation of nonpigmented ciliary epitheliumhas been described from which tissue can be processed rapidly from subsequent experiments. Separation of the intact rabbit NPE layer by [29], and, more recently, of both the NPE and PE layers have been described [75]. In the latter, separation of the dual layers of the rabbit ciliary epithelium utilizes incubation of freshly dissected ciliary bodies in Hepes buffered Ringer's solution with the $Ca^{2+}$ reduced to 30 µM. Upon spontaneous separation of the NPE layer, the further reduction of external $Ca^{2+}$ to sub-µM (by the addition of EGTA) resulted in spontaneous dissociation of the PE layer [75]. The viability of the preparations was confirmed in subsequent physiological experiments.

Two types of experiments are performed. First, quantitative immunoblotting is performed to assess the total levels of vacuole $H^+$-ATPase subunits in cytosolic and membrane fractions in response to drugs. Secondly, incorporation of $^{35}S$-methionine and immunoprecipitation assesses the rate of synthesis of the ATPase subunits.

3. Western immunoblotting:
Rabbit iris/ciliary body sections from freshly sacrificed animals are harvested on ice, and the iris is removed so that only ciliary body (both muscle and ciliary epithelium) remain. Ciliary bodies are incubated in modified oxygenated Ringer's buffer for 30 minutes at 37° C., washed, and treated with drugs as identified above for times ranging from 5 minutes to 1 hour in oxygenated modified Ringer's buffer. For experiments involving cultured cells, cells are grown to confluency in the presence of 5% FCS, and then grown for an additional 24 hours in serum free media prior to harvesting. Cytoplasmic and membrane homogenates prepared by homogenizing the cells in a hypotonic lysis buffer (2 mM HEPES/2 mMEDTA/protease inhibitors/pH 7.4), is followed by differential centrifugation. The low speed pellet (100,000× g, 10 min) consisting of nuclei and unbroken cells is discarded, while the high speed pellet (100,00× g, 40 min) representing total cellular membranes and the high speed supernatant is retained. Proteins of the cytosol and membrane fractions is separated by SDS-PAGE, electrophorectically transferred to PVDF membranes (Immobilon P). The blots are first incubated with Tris buffered saline containing 0.1% Tween 20 and 5% nonfat dry milk (to block nonspecific binding), and then with antibodies selective for $H^+$-ATPase subunits. After washing and incubating with secondary antibody labeled with horse-radish peroxidase, the bands are visualized by enhanced chemiluminescence and quantitated with a Bio-Rad Scanning Densitometer.

4. Synthesis:
Treated and control tissues or cells are incubated in methionine free media for 30 min, and then labeled with $^{35}S$-methionine for various times (1–24 hrs). The cells/tissue is washed and cytosol and membrane fractions prepared as above. The membranes are solubilized with 1.5% nonyl glucoside and 0.6% CHAPS. Total radioactivity incorporated into protein in the cytosol and solubilized membrane is measured by TCA precipitation, and aliquots containing equal numbers of TCA-percepitatible counts are taken from the control and treated tissues for immunoprecipitation. The aliquots of labeled tissue extract are incubated overnight with monoclonal anti $H^+$-ATPase IgG (or MOPC as control) and protein-A sepharose beads [80]. Following 3 washes in PBS, the antigen is eluted from the beads in SDS-PAGE sample buffer, separated by electrophoresis on a 7–12% gradient SDS-polyacrylamide gel. The gels are processed for fluorography (using ENHANCE, NEN), dried, and exposed to X-ray film. Bands are quantitated using the Bio-Rad Scanning Densitometer.

EXPERIMENT 10

Specific vacuolar $H^+$-ATPase activity and spectrophotometric assessment of proton translocation utilizing acridine orange is used to study regulation of the native enzyme in response to drugs and inhibitors.

The function of vacuolar $H^+$-ATPase in microsomes is generally assessed by the use of 2 assays which are consonant yet distinct. First, specific vacuolar $H^+$-ATPase activity is studied in membrane vesicles by measuring the dephosphorylation of $[\gamma^{32}P]$ ATP in the presence and absence of various inhibitors ($H^+$-ATPase is vanadate and azide resistant and N-ethylmalemide and bafilomycin sensitive). Secondly, the ability of the vacuolar $H^+$-ATPase to translocate protons is assessed spectrophotometrically by use of acridine orange. Both activities of ciliary epithelial vacuolar $H^+$-ATPase in response to drugs which have a) altered the translocation Vacuolar $H^+$-ATPase in vivo and in vitro and b) inhibitors of vacuolar $H^+$-ATPase such as oligonucleotides that we have shown lower intraocular pressure was assessed.

1. Microsome preparation:

All steps are carried out at 4° C. unless otherwise noted. Microsomes are prepared from isolated rabbit ciliary epithelium, SV4—transformed PE and NPE cells at confluency by aspirating the media, washing the plated cells with iced-cold PBS buffer followed by incubation in ice-cold lysis buffer (2 mM Hepes, 2 mM EDTA, 0.5 mM EGTA, pH 7.4). Cell lysates is then removed from tissue culture flasks by scraping with a rubber policeman. The cells are further lysed with 40 strokes in a tight fitting glass-glass homogenizer. Intact cells and nuclear fragments were removed by low speed centrifugation (5 min 1000× g). Membrane fragments containing microsomes are then sedimented by high speed centrifugation (20 min at 40,000× g), resuspended in tissue buffer (10 mM Tris, 1 mM EDTA, 0.5 mM EGTA, pH 7.4), sedimented a second time and resuspended in the same tissue buffer. Microsomes are stored in tissue buffer (2.5 mg/ml) at −80° C. until use. The supernatant fraction containing cytosol is stored at −80° C. until use. When the native tissue is the source for the preparation of microsomes, the tissue is first homogenized 1:4 (w/v) in buffer containing 2 mM Hepes, 2 mM EDTA, 0.5 mM EGTA, pH 7.4, 5 mM DTT, and 5 mM $N_aN_3$. The homogenate is centrifuged at 6,000× g for 15 min, and the supernatant is centrifuged at 40,000× g for 1 hour. The microsomal pellet is washed once with buffer containing 2 mM Hepes, 2 mM EDTA, 0.5 mM EGTA, pH 7.4, and then resuspended in the same buffer and stored at −80° C. until use.

2. Assay of Vacuolar $H^+$-ATPase activity:

Steady state ATPase activity from ciliary epithelial tissue and cultured cells is measured by colorometric assay of inorganic phosphate as described [8] or formation of radioactive $P_i$ from $[\gamma-^{32}P]$ ATP as described by Grubmeyer and Penefsky [20]. The standard mixture for inorganic phosphate assay contains 25 mM MOPS, pH 6.7, 5 mM $Na_2ATP$, 5 mM $MgCl_2$, and 0.02% asolectin in a total volume of 1.0 ml. Assays are carried out at 30° C. for 5–30 min (ATP hydrolysis less than 5%) and is terminated by the addition of trichloroacetic acid to a final concentration of 1.0%. The reaction mixture for radioactive measurement of $P_1$ contains 20 mM Tris HCl, pH 7.5, 2 mM $[\gamma-_{32}P]$ ATP in the presence of or absence of $MgCl_2$ at 25° C. for various times. The reaction is stopped by adding an equal volume of cold 40% trichloroacetic acid (w/v) containing 5 mM $H_3PO_4$ and 1 mM ATP. Then bovine serum albumin (0.7 mg/ml) is added and the mixture is kept on ice for 10 min and centrifuged for 5 min at 13000× g. The precipitate is washed with 15% trichloroacetic acid containing 1.7 mM $H_3PO_4$ and 0.3 mM ATP. Finally the precipitate is dissolved in 150 ml of 1N NaOH and its radioactivity measured in liquid scintillation counter. One unit of enzyme are defined as the amount hydrolyzing 1 μmol of ATP/min.

3. Proton translocation assay:

The acridine orange fluorescence-quenching assay [46, 47] is used to monitor transport. Ciliary epithelial membrane vesicles (150 μg) are added to 2 ml of 10 mM Tris HCl, pH 7.0, 50 mM KCl, 5 mM , and 2.5 μM acridine orange in a 3.5 ml fluorescence cuvette. These conditions have been previously shown to be optimal for measurement of pH gradient formation [47]. Fluorescence quenching (ATP induced uptake of acridine orange) is initiated by the addition of 5 mM $MgSO_4$ plus 5 mM ATP and is monitored spectrofluorometrically as previously described [86]. Since the protonated form of acridine orange is less permeable than the weak base, the development of an acid pH in the vesicles lead to an accumulation of the dye. Steady state fluorescence quenching measurement is performed as described previously [48]. All transport assays are performed at room temperature.

EXPERIMENT 11

Genetic targeting of vacuolar $H^+$-ATPase activity in the ciliary epithelium.

1. Inactivation of vacuolar $H^+$-ATPase activity using oligonucleotides

Gene expression is controlled by the products of regulatory genes. According to a great number of studies in the past 30 years, the products of such genes were determined to be proteins termed activators or repressors. Recently, naturally occurring regulatory genes have been discovered that direct the synthesis of RNA which can directly control gene expression. These newly discovered RNA repressors are highly specific inhibitors of gene expression. The regulatory RNA contains a sequence that is complementary to the target RNA, and binding of the two RNA's occurs by base pairing. The term antisense RNA is used to designate this regulatory RNA. The finding that antisense RNA can inhibit gene expression in natural systems is very useful in the development of strategies to artificially regulate the function of the cloned gene product of vacuolar $H^+$-ATPase in the ciliary epitheliumusing antisense RNA. By the manipulations of antisense RNA, complementary to a chosen mRNA can be synthesized in vitro or in vivo and injected or transfected into cells and may be used to inhibit the expression of the respective target gene. The function of the endogenous genes has been suppressed by artificial antisense RNA [78]. In higher organisms, direct microinjection of antisense RNA into cells has also resulted in the specific inhibition of gene expression [19].

To inactivate the function of the ciliary epithelial vacuolar $H^+$-ATPase, the SV40-transformed bovine-derived pigmented (PE), human derived non-pigmented (NPE) ciliary epithelial cell lines and rabbit nonpigmented ciliary epithelium grown in primary culture is used as cell models for the transfection of antisense RNA. Transfection to introduce antisense RNA into ciliary epithelial cells was employed. First, the genes from native tissue and the cloned cell lines are cloned to ascertain the sequences to which the oligonucleotides are directed.

Several current methods of transfection were utilized. The newly synthesized enzyme was inhibited with antisense such that sequential applications may be necessary to be clinically effective. Many eye drops used in glaucoma obey 1st order kinetics following topical delivery and thus need to be reapplied 2, 3 or even 4 times a day. Thus, specificity of antisense directed against vacuolar $H^+$-ATPase was demonstrated.

To inactivate the function of the cloned ciliary epithelial vacuolar $H^+$-ATPase gene, the full length cDNA cloned into the plasmid pBluscript KS+ or the synthesized deoxyoligonucleotide targeted toward the initiation codon of the 56 kD subunit of ciliary epithelial vacuolar $H^+$-ATPase is used. Sense and antisense RNA is synthesized in vitro using the linearized recombinant pBluscript KS+ plasmid carrying the full length gene for ciliary epithelial vacuolar $H^+$-ATPase and the T3 and T7 RNA polymerases, respectively. The sense and antisense RNA is transfected into the SV40-transformed bovine-derived pigmented (PE) and human derived non-pigmented (NPE) ciliary epithelial cell lines.

Oligonucleotides are used which cause sequence specific inhibition of the translation of the mRNA. Several classes of a 18–28 base length oligonucleotides were employed that initially was targeted at the initiation codon region. These include orthothioate oligonucleotides, or oligonucleotides that have undergone "backbone" modifications such as dithioates, phosphodiesters (PO) [58], phosphorothioates (PS), chimeras (mixed PO.PS cholesteryl) [30, 56]. By use of this strategy, maximize intracellular oligonucleotide retention (by slowing the exocytosis rate), and to minimize nuclease digestion was demonstrated. As controls, multiple (at least four) oligonucleotides of identical length and base composition but with altered sequence were employed. GenBank is searched for potential homologies to other targets.

1. Construction of vectors for synthesis of RNA:

Vectors capable of generating RNA molecules containing sequences complementary to ciliary epithelial vacuolar $H^+$-ATPase are constructed by standard recombinant DNA techniques. The DNA that contains the coding sequences in frame within the 5' and 3' untranslated sequence of human adult β-globin gene (for polyA+ signals and gene splicing) is ligated into pBluscript KS+. Confirmation of recombinants is described [52]. Sense RNA is synthesized with T3 RNA polymerase and linearized recombinant plasmid. Antisense RNA is synthesized with T7 RNA polymerase.

2. Transfection of RNA:

The transfection of antisense RNA in isolated ciliary epithelium, SV40-transformed bovine-derived pigmented (PE), human derived-non-pigmented (NPE) ciliary epithelial cell lines is accomplished by the following techniques.

A. Transfection of cells with RNA using Lipofectin reagent:

A common way to introduce RNA molecules into eukaryotic cells is transfection using Lipofectin reagent (available from Promega) [10, 69]. This method is used for both adherent and suspension cells. Lipofectin reagent is a liposome formulation of a cationic and a renal lipid that interacts with DNA to form a lipid-DNA complex. The fusion of the lipid-DNA complex with cells results in uptake of nucleic acids. For optimal transfection with Lipofectin reagent, several parameters are important, such as, the culture medium, the concentration of nucleic acid, the concentration of Lipofectin reagent, and the incubation time. These parameters optimized first to increase the efficiency of uptake of the nucleic acid. Common problems encountered with Lipofectin reagent are cell death, low transfection efficiency, and precipitation of the Lipofectin reagent-DNA complex.

B. Transfection of cells with RNA using gene electroporator:

The cultured cells are transformed with vectors expressing antisense and sense RNA or transfected with antisense and sense RNA using gene electroporator as described [52]. Electroporation induces a transmembrane potential which results in the formation of pores that are large enough to allow DNA and RNA molecules or small oligonucleotides to enter cell. Due to its ease of use, reproducibility and high frequency of transformation, electroporation has become the method of choice for introducing many types of molecules into different cell types [35, 53, 81].

C. Protoplast fusion transfection:

This technique achieves the transfer of plasmid DNA from bacteria expressing the antisense RNA for the target gene into the mammalian cell by PEG-mediated fusion of bacterial spheroplasts with the mammalian cells. Any bacterial strains should work but the conditions for generating spheroplasts vary from strain to strain. Protoplast preparation is carried out after treating the cells with lysozyme [4]. The protoplast preparation is incubated with cultured cells in the presence of 50% PEG at 37° C. and then selected against the antibiotics. Cell fusion is carried out as described. This technique is used to introduce plasmid DNA into cells that are difficult to transfect or when it is more convenient to reintroduce DNA without going through a plasmid DNA preparation. Electroporation is much simpler than protoplast fusion but it is sometimes difficult to find just the right conditions for transfection. For protoplast fusion the biggest variable seems to be the survival of the mammalian cells to the procedure. This can be overcome to a certain extent by adding more cells.

D. Transfection using Retroviral vectors: Retroviral infection can be used as an alternative to nucleic acid transfection for the introduction of foreign genetic material into cells [25]. This approach also has some advantages, such as, high gene transfer efficiency, infection of several cell types which is refractory to transfection, ability to study the effects of introduced genes in total cell populations and not only in relatively rare transfectants. Plasmid DNA corresponding to the engineered vector with helper virus plasmid DNA can be transfected into normal NIH3T3 cells. Transfected clones can then be selected with the appropriate antibiotic. The cells are then tested for viral production by replacing the antibiotic-containing medium with normal medium and continuing the incubation for 16–18 hours. Virus is then collected from cells by passing through 0.45 μm filter and is stored on ice and used immediately to infect other cells. Infection is done by adding virus to cells in the presence of polybrine(2–8 μg/ml) and incubated for 2 hours at 37° C. Cells is allowed to grow for 24–36 hours in fresh medium and then can be split into selective medium.

3. Assessment of antisense efficacy:

In order to evaluate the assessment of antisense in blocking vacuolar $H^+$-ATPase, ATPase assays which measure the liberation of inorganic $^{32}P_i$ from $\lambda[^{32}P]$-ATp were performed, and assays that measure proton translocation with the spectrophotometric use of acridine orange as describe hereinabove. These experiments are able to effectively determine whether or not vacuolar ATPase in microsomes have been effected by antisense, but one of the main tents of this application is that plasma membrane bound vacuolar $H^+$-ATPase in the ciliary epithelium effects the transcellular movement of ions, particularly bicarbonate. Spectrofluorometry on ciliary epithelial cells in culture following antisense transfection were performed to assess intracellular pH in response to conditions described hereinabove.

REFERENCES

1. Agrawal, S., et al., (1988) Proc. Natl. Acad. Sci. U.S.A. 85:7079–7083.
2. Agrawal, S., and Sarin, P. S., (1991) Adv. Drug. Del. Res. 6:251–270.
3. Bode, D., et al., (1993) J. Pharm. Exp. Ther. 267:1286–1291.
4. Bothwell A, et al., (1990) Methods For Cloning And Analysis Of Eukaryotic Genes, Jones and Bartlett, Boston.
5. Bowman, B. J., et al., (1988) Proc. Natl. Acad. Sci. U.S.A. 85:7972–7076.
6. Civan, M. M., et al., (1992) Exp. Eye. Res. 54:181–191.
7. Coca-Prados, M., and Lopez-Briones L., (1987) Biochem. Biophys. Res. Comm. 145:460–466.
8. Dryer, R. L., et al., (1857) J. Biol. Chem. 225:177–183.
9. Fain, G. L., et al., (1988) Invest. Ophthalmol. Vis. Sci. 29:788–794.
10. Flenger, P. L., et al., (1987) Proc. Natl. Acad. Sci. U.S.A. 84:7413–7418.
11. Flugel, C., and Lutjen-Drecoll E. (1988) Histochemistry 88:613–21.
12. Friedland, B. R., and Maren, T. H., (1989) The Glaucomas, St. Louis, The C.V. Mosby Co., 1:539–550.
13. Gardner, S.K., (1988) Ocular Therapy Report 1:13–20.
14. Gaul, G. R., and Brubaker, R. F., (1986) Invest. Ophthalmol. Vis. Sci. 27:1331–1335.
15. Ghosh, S., et al., (1988) J. Biol. Chem. 265:2935–2940.
16. Ghosh, M.K., et al., (1993) Anti-Cancer Drug Design 8:15–32.
17. Ghosh, S., et al., (1990) J. Biol. Chemo 265:2935–2940.
18. Gluck, S., et al., (1982) J. Biol. Chem. 257:9230–9233.
19. Green, P.J., et al., (1986) Ann. Rev. Biochem. 55:569–597.
20. Grubmeyer, C., and Penefsky, H. S., (1981) J. Biol. Chem. 256:3718–3727.
21. Harvey, W., (1992) J. Exp. Biol. 172:1–17.
22. Hays, S. R., and Alpern, R. J., (1991) J. Gen. Physiol. 98:791–813.
23. Helbig, H., et al., (1988) Ophthalmol. 85:42–45.
24. Hirsch, S., et al., (1988) Proc. Natl. Acad. ScI. U.S.A. 85:3004–3008.
25. Huang, H. S. et al., (1988) Science 242:1563–1566.
26. Iverson, P., (1991) Anti-Cancer Drug Des. 6:531–538.
27. Johnson, F., and Maurice, D., (1984) Exp. Eye. Res. 39:791–805.
28. Jones, R. F., and Maurice, D. M., (1966) Exp. Eye. Res. 5:208–220.
29. Jumblatt, M. M., et al., (1991) J. Exp. Eye. Res. 52:229–232.
30. Krieg, A., et al., (1993) Proc. Natl. Acad. Sci. U.S.A. 90:1048–1052.
31. Krupin, T. K., et al., (1991) J. Exp. Eye. Res. 53:709–716.
32. Krupin, T. K., et al., (1984) J. Exp. Eye. Res. 38:115–123.
33. Lee, C., et al., (1989) J. Exp. Eye. Res. 48:733–743.
34. Lestinger, R., U.S. Pat. No. 4,958,013, issued Sep. 18, 1990; Rosenberg, P., et al. PCT International Application No. PCT/US92/05305, filed Jun. 23, 1992; Maggi, A, and Nicolin, A., PCT International Application No. PCT/EP92/01745, filed Jul. 29, 1992.
35. Ley, T., and Ulrich, J. M., (1990) Blood 75:990–999.
36. Matsukura, M., et al., (1987) Proc. Natl. Acad. Sci. U.S.A. 84:7706–7710.
37. Mellman, I., et al., (1986) Ann. Rev. Biochem. 55:663–700.
38. Moriyama, Y., and Nelson, N., (1988) FEB. 234:383–386.
39. Moriyama, Y., and Nelson, N. (1987) J. Biol. Chem. 262:9175–9180.
40. Munroe, W. P., et al., (1985) Drug Intell. and Clin. Pharm. 1.9:85–89.
41. Nelson, N., (1992) J. Exp. Biol. 172:19–27.
42. Nelson, N., (1992) Biochem. Biophys. Acta. 1100:109–124.
43. Nelson, N., (1992) Curro Biol. 4:654–660.
44. Nelson, N., et al., (1992) Proc. Natl. Acad. Sci. U.S.A. 89:3541–3545.
45. Okami, T., et al., (1989) J. Histochem. Cytochem. 37:1353–61.
46. Perlin, D.S., et al., (1983) J. Biol. Chem. 258:9793–9800.
47. Perlin, D.S., et al., (1984) J. Biol. Chem. 259:7884–7892.
48. Perlin, D. S., et al., (1986) Arch. Biochem. Biophys. 248:53–61.
49. Puopolo, K., et al., (1991) J. Biol. Chem. 266:24565–24572.
50. Puopolo K., et al., (1992) J. Biol. Chem. 267:3696–3706.
51. Ratajczak, M. Z., et al, (1992) Proc. Natl. Acad. Sci. U.S.A. 89:11823–11827.
52. Sambrook, J., and Fritsch, E.F., (1989) Molecular Cloning: A Laboratory Manual, 2nd ed. Cold Spring Harbor Laboratory, Cold Spring Harbor, N.Y.
53. Saunders, J., et al., (1989) J. Biotechniques 7:1124–1131.
54. Shewmaker et al., U.S. Patent No. 5,107,065, issued Apr. 21, 1992.
55. Socci, R. R., and Delamere, N. A., (1988) Invest. Ophthalmol. Vis. Sci. 29:1866–1870.
56. Stein, C. A., et al., (1991) R. Blochem. 30:2439–2444.
57. Stein, C. A., et al., (1991) Pharmac. Ther. 52:365–384.
58. Stein, C. A., et al. (1993) Biochemistry 32:4855–4861.
59. Stein, C. A., and Cohen, J. S., (1993) Cancer: Principles and Practice of Oncology, Lippincott, Philadelphia, pp. 80–97.
60. Stein, C. A., et al., (1993) Biochem. 32:4855–4561.
61. Thomas, J.A., et al., (1979) Biochem. 18:2210–2218.
62. Townsend, D.J., and Brubaker, R. F., (1980) Invest. Ophthalmol. 19:256–266.
63. Tullis, U.S. Pat. No. , issued Jun. 11, 1991.
64. Uhlmann, E., and Peyman, A., (1990) Chem. Rev. 90:544–579.
65. Usukura, J., et al., (1988) Invest. Ophthalmol. Vis. Sci. 29:606–614.
66. VanBuskirk, M., (1980) Ophthalmol. 87:447–450.
67. Wang, Z. Q, and Gluck, S., (1990) J. Biol. Chem. 265:21957–21965
68. Wax, M. B., (1992) Pharmacology of Glaucoma, Williams and Wilkins, Baltimore, pp. 184–210.

69. Weiner, D. B., et al., (1988) Proc. Natl. Acad. Sci. U.S.A., 86:6077–6081.
70. Werner, G., et al., (1984) J. Antibiot. 37:110–117.
71. Wiederholt, M., and Zadunaisky, J. A., (1987) Invest. Ophthaimol. Vis. Sci. 28:1353–1356.
72. Wiederholt, M., and Zadunaisky, J. A., (1986) Pflugers Arch. 407:S112–115.
73. Wolosin, J. M., et al., (1991) Exp. Eye. Res. 52:397–407.
74. Wolosin, J. M., et al., (1989) Ann. N.Y. Acad. Sci. 574:131–133.
75. Wolosin, J. M., et al., (1993) Exp. Eye. Res. 56:401–409.
76. Yantorno, R. E., et al., (1992). Am. J. Physiolo 262:C501–C509.
77. Yilla, M., et al., (1988) J. Biol. Chem. 268:19092–19100.
78. Yokoyama, K., and Imamoto, F., (1987) Proc. Natl. Acad. Sci. U.S.A. 84:7363–7367.
79. Yoshimori, T., et al., (1991) J. Biol. Chem. 266:17707–17712.
80. Yurko, M. A., and Gluck, S., (1987) J. Biol. Chem. 262:15770–15779.
81. Zealey, G., et al., (1988) FEMS Miocrobiol Lett. 56:123–126.
82. Zhao, Qiuyan, et al., (1993) Antisense Research and Development 3:53–66.
83. Zimmerman, T. J., et al., (1983) J. Surv. Ophthalmol. 28:243–249.

What is claimed:

1. A method of treating glaucoma which comprises administering to a subject an effective amount of an oligonucleotide which may be substituted or modified in its phosphate, sugar, or base, so as to decrease intraocular pressure and thereby treat the glaucoma.

2. A method of claim 1, wherein aqueous humor formation in the eye is decreased.

3. A method of claim 1, wherein aqueous outflow from the eye is facilitated.

4. The method of claim 1, wherein the oligonucleotide is a oligodeoxynucleotide.

5. The method of claim 1, wherein the substituted oligonucleotide is phosphorothioate.

6. The method of claim 5, wherein the phosphorothioate is stereo regular.

7. The method of claim 5, wherein the phosphorothioate is stereo non-regular.

8. The method of claim 1, wherein the substituted oligonucleotide is a phosphorodithioate.

9. The method of claim 1, wherein the oligonucleotide is a homopolymer.

10. The method of claim 1, wherein the oligonucleotide is a heteropolymer.

11. The method of claim 1, wherein the oligonucleotide is further linked to a 3' or 5'-cholesteryl moiety.

12. The method of claim 1, wherein a 5' or 3' end of the oligonucleotide is further linked with an intercalating agent, a cross-linker, an artificial endonuclease, a lipophilic carrier or a peptide conjugate, or combination thereof.

13. The method of claim 1, wherein the oligonucleotide is conjugated to a carbohydrate or glycan.

14. The method of claim 1, wherein the oligonucleotide is conjugated to a sulfated carbohydrate.

15. The method of claim 1, wherein the type of glaucoma is selected from the group consisting of acute glaucoma, absolute glaucoma, chronic glaucoma, congenital glaucoma, juvenile glaucoma, narrow angle glaucoma, open angle glaucoma, or simplex glaucoma.

16. The method of claim 1, wherein the administration is a method comprising topical, oral, intravenous, intramuscular, intratracheal, or subcutaneous administration.

17. The method of claim 1, wherein the administration comprises topically applying the solution into the eye of a subject.

18. The method of claim 1, wherein the effective amount is in a range of 1 nM to 10 mM.

19. The method of claim 18, wherein the effective amount is in a range of 0.1 mM to 0.5 mM.

20. The method of claim 1, wherein the subject is a mammal.

21. The method of claim 20, wherein the mammal is a human.

22. The method of claim 20, wherein the mammal is a horse, pig, rabbit, monkey, cat, or dog.

* * * * *